US010672247B2

(12) United States Patent
Yang et al.

(10) Patent No.: US 10,672,247 B2
(45) Date of Patent: Jun. 2, 2020

(54) VEHICLE OCCUPANT DETECTION DEVICE

(71) Applicant: XANDAR KARDIAN, Seoul (KR)

(72) Inventors: Sun Jong Yang, Gangwon-do (KR); Jeong Woo Choi, Seoul (KR)

(73) Assignee: Xandar Kardian, Seoul (KR)

( * ) Notice: Subject to any disclaimer, the term of this patent is extended or adjusted under 35 U.S.C. 154(b) by 0 days.

(21) Appl. No.: 16/437,156

(22) Filed: Jun. 11, 2019

(65) Prior Publication Data

US 2020/0118409 A1 Apr. 16, 2020

(30) Foreign Application Priority Data

Oct. 16, 2018 (KR) .......................... 10-2018-0123168

(51) Int. Cl.
*B60R 21/01* (2006.01)
*G08B 21/02* (2006.01)
*B60N 2/00* (2006.01)
*A61B 5/024* (2006.01)

(52) U.S. Cl.
CPC .......... *G08B 21/0211* (2013.01); *B60N 2/002* (2013.01); *A61B 5/024* (2013.01)

(58) Field of Classification Search
CPC ..... G08B 21/0211; B60N 2/002; A61B 5/024; B60R 21/01; B60R 21/01512; B60R 21/01534; B60R 2021/01088; B60K 37/02; B60Q 9/00
See application file for complete search history.

(56) References Cited

U.S. PATENT DOCUMENTS

| 6,753,780 | B2 * | 6/2004 | Li | B60N 2/002 180/271 |
| 7,276,030 | B2 | 10/2007 | Takasuka | |
| 8,892,302 | B1 * | 11/2014 | McDonald | G08B 21/24 701/36 |
| 9,403,437 | B1 * | 8/2016 | McDonald | B60K 37/02 |

(Continued)

FOREIGN PATENT DOCUMENTS

| JP | 2017181225 A | 10/2017 |
| KR | 1020040048898 A | 6/2004 |

(Continued)

OTHER PUBLICATIONS

European Search Report dated Aug. 27, 2019 for Application No. 19180272.7.

(Continued)

*Primary Examiner* — An T Nguyen
(74) *Attorney, Agent, or Firm* — Paul D. Bianco; Fleit Intellectual Property Law

(57) ABSTRACT

A vehicle occupant detection device according to an embodiment of the present invention is provided. The vehicle occupant detection device includes a sensor unit disposed in a vehicle to detect biometric information of an occupant located in a front seat of the vehicle and a rear seat of the vehicle, a control unit analyzing the biometric information measured by the sensor unit, and an output unit outputting a warning message on the basis of the information analyzed by the control unit, wherein the control unit determines that the occupant located in the rear seat is in a dangerous state when the biometric information is not detected in the front seat but detected in the rear seat.

14 Claims, 8 Drawing Sheets

(56) References Cited

U.S. PATENT DOCUMENTS

| | | | |
|---|---|---|---|
| 9,403,501 B2* | 8/2016 | Teng | B60N 2/002 |
| 9,671,492 B2* | 6/2017 | Diewald | G01S 7/354 |
| 10,457,161 B2* | 10/2019 | Lu-Dac | A61B 5/4809 |
| 2002/0029103 A1* | 3/2002 | Breed | B60N 2/002 |
| | | | 701/45 |
| 2007/0193811 A1* | 8/2007 | Breed | B60R 21/01536 |
| | | | 180/271 |
| 2009/0261979 A1* | 10/2009 | Breed | B60J 10/00 |
| | | | 340/576 |
| 2015/0129343 A1* | 5/2015 | Teng | B60N 2/002 |
| | | | 180/271 |
| 2016/0001728 A1* | 1/2016 | Schrabler | B60R 21/01534 |
| | | | 342/28 |
| 2017/0158202 A1 | 6/2017 | Yang | |
| 2018/0099592 A1 | 4/2018 | Curry | |

FOREIGN PATENT DOCUMENTS

| | | |
|---|---|---|
| KR | 101792949 B1 | 11/2017 |
| KR | 1020180024771 A | 3/2018 |
| KR | 10-2018-0058915 A | 6/2018 |
| KR | 2018 0110825 A | 10/2018 |

OTHER PUBLICATIONS

Korean Office Action dated Nov. 27, 2018 for Application No. 10-2018-0123168, 16 pages.
Korean Final Office Action dated Mar. 6, 2019 for Application No. 10-2018-0123168, 5 pages.
Korean Notice of Allowance dated May 20, 2019 for Application No. 10-2018-0123168, 4 pages.

* cited by examiner

FIG. 1
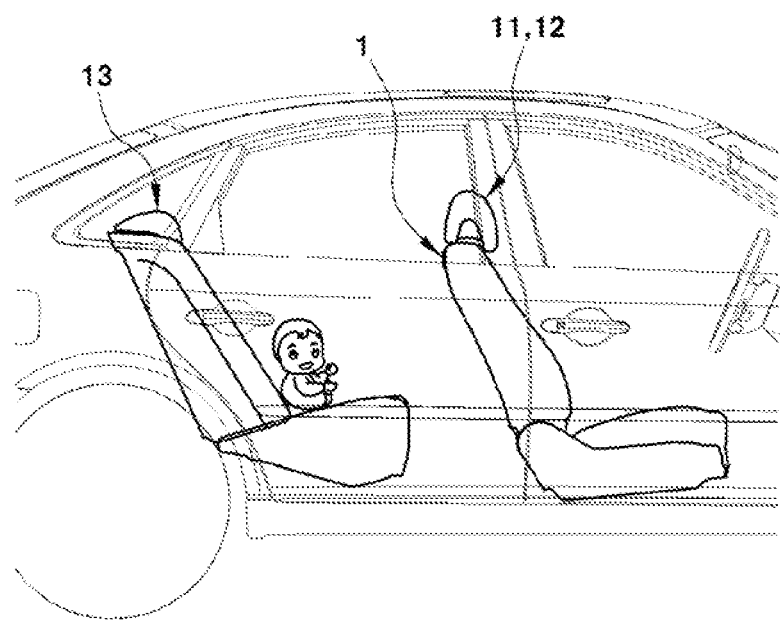
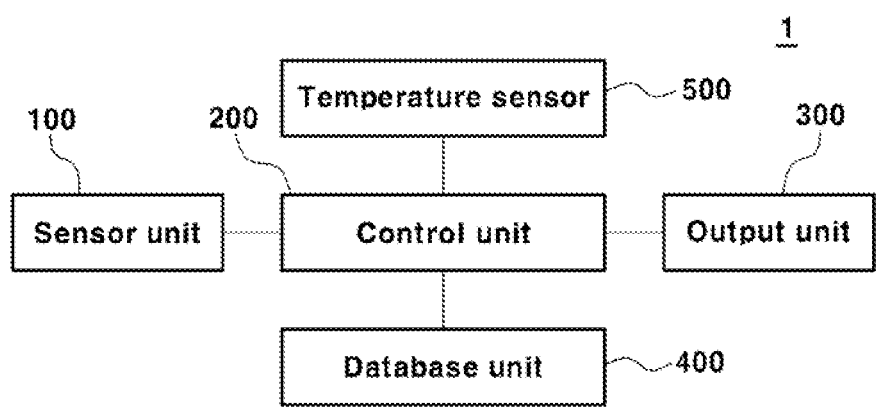
FIG. 2

VEHICLE OCCUPANT DETECTION DEVICE

CROSS REFERENCE TO RELATED APPLICATION

The present application claims priority to Korean Patent Application No. 10-2018-0123168, filed Oct. 16, 2018, the entire contents of which is incorporated herein for all purposes by this reference.

BACKGROUND OF THE INVENTION

Field of the Invention

The present invention relates generally to a vehicle occupant detection device and, more particularly, relates to a vehicle occupant detection device for preventing an infant from being left in a rear seat of a vehicle.

Description of the Related Art

Recently, accidents where infants are left unattended in a vehicle and then die or become unconscious have being increasingly occurring. When the outdoor temperature is 21 degrees Celsius, a temperature in the vehicle can heat up to 49 degrees Celsius in 10 minutes, and in summer, the indoor temperature of the vehicle can be increased up to about 80 degrees Celsius in an hour. Infants may experience fatal accidents when exposed to these extreme conditions compared to adults.

Therefore, when an infant is left alone in a vehicle, there is a need for a system that enables a guardian or another person to be notified of the situation. Techniques for detecting a presence of infants in a rear seat have been developed by installing a decompression sensor in the rear seat or installing a thermal sensor inside the vehicle. However, since the indoor temperature of the vehicle can be increased to up about 80 degrees Celsius in the summer, there is a problem that the decompression sensor and the thermal sensor may not operate properly. In addition, there is a problem that there is no way to distinguish a case that the infant and his/her guardian are present together in the vehicle from a case that the infant is left alone in the vehicle.

SUMMARY OF THE INVENTION

The present invention has been made keeping in mind the above problems occurring in the related art, and an object of the present invention is to provide a vehicle occupant detection device for detecting infants left inside a vehicle.

The present invention provides a vehicle occupant detection device for detecting a presence of an infant left alone in a vehicle by distinguishing a case where an infant and his/her guardian are present together from a case where an infant is alone.

In order to accomplish the above object, a vehicle occupant detection device according to an embodiment of the present invention is provided. The vehicle occupant detection device includes a sensor unit disposed in a vehicle to detect biometric information of an occupant located in a front seat of the vehicle and a rear seat of the vehicle; a control unit analyzing the biometric information measured by the sensor unit; and an output unit outputting a warning message on the basis of the information analyzed by the control unit, wherein the control unit determines that the occupant located in the rear seat is in a dangerous state when the biometric information is not detected in the front seat but detected in the rear seat.

According to an example, the biometric information may be at least one of heart rate, movement, or respiration of the occupant.

According to an example, the sensor unit may be any one of an impulse-radio ultra-wideband (IR-UWB) communication sensor, a Lidar, a frequency modulated continuous wave (FMCW) radar, and a Doppler radar.

According to an example, the sensor unit may be attached to a rear surface of the front seat, and the rear surface may be a surface facing the front seat in the rear seat.

According to an example, the sensor unit may measure the biometric information generated in a first area and a second area, in which the first area is present in a direction facing the rear seat in the front seat and the second area is present in a direction opposite to the first area.

According to an example, the front seat may mean a driver's seat; and the control unit may determine whether a first occupant located in the driver's seat and a second occupant located in the rear seat are present or not and control the output unit to output the warning message when the first occupant is not present and the second occupant is present.

According to an example, the vehicle occupant detection device may further include a database unit storing information on repetitive movements generated inside the vehicle, in which the control unit determines that information that is the same as the information stored in the database unit among the biometric information measured by the sensor unit is not the biometric information of the occupant.

According to an example, the repetitive movement may mean moving on a regular cycle.

According to an example, the control unit may control the output unit to output the warning message when determining that the occupant located in the rear seat is in a dangerous state.

According to an example, the output unit may include a warning unit outputting the warning message through a warning sound or a warning light; and a communication unit transmitting the warning message to a terminal located outside the vehicle through a wireless communication method.

According to an example, the control unit may output a signal containing the warning message to the outside of the vehicle through the sensor unit, and the signal may be the same as a signal that the sensor unit outputs to measure the biometric information.

According to an example, a range in which the sensor unit detects the biometric information may be set in advance according to a size of the vehicle.

According to an example, the sensor unit may output a signal toward the occupant and receive the signal reflected from the occupant to measure the biometric information of the occupant, and the control unit may determine whether the occupant is an adult or an infant through the reflected signal.

According to an example, the database unit may compare the reflected signal with a signal pattern learned through machine learning, and the control unit may determine whether the occupant is an adult or an infant using the signal pattern matched with the reflected signal.

According to an example, the control unit may determine the number of the occupants located in the rear seat when the biometric information is not detected in the front seats but detected in the rear seat, and the control unit may determine whether the adult is present or not among a plurality of occupants.

According to an example, the control unit may control the output unit to output the warning message when the adult is not present among the occupants, the control unit may control the output unit not to output the warning message when the adult is present among the occupants.

According to an example, the vehicle occupant detection device may further include a temperature sensor disposed within the vehicle, wherein the control unit may apply an allowable time from a point of time when the biometric information is not detected in the front seat but detected in the rear seat to a point of time when the warning message is output, differently to each of a case in which a value of the temperature sensor is equal to or higher than a predetermined temperature and a case in which the value is lower than the predetermined temperature.

According to an embodiment of the present invention, when no occupant is present in the front seat, the vehicle occupant detection device can determine that infants located in the rear seat are in a dangerous state and thus output a warning message. Accordingly, the vehicle occupant detection device can determine when infants are left alone in the vehicle.

According to an embodiment of the present invention, since the vehicle occupant detection device uses a Lidar or an impulse radio ultra-wideband (IR-UWB) communication sensor, the occupant's biometric information can be accurately measured even inside a vehicle at a high temperature.

According to an embodiment of the present invention, even if there is no configuration for outputting a separate warning message, the vehicle occupant detection device can output an ultra-wideband signal to the outside of the vehicle so that people outside the vehicle can know that the infant is left alone in the vehicle. Accordingly, it is possible to reduce the cost of implementing the device for detecting the infant left alone in the vehicle and thus to make the device compact.

BRIEF DESCRIPTION OF THE DRAWINGS

The above and other objects, features and other advantages of the present invention will be more clearly understood from the following detailed description when taken in conjunction with the accompanying drawings, in which:

FIG. 1 is a view showing the inside of a vehicle in which a vehicle occupant detection device according to an embodiment of the present invention is installed;

FIG. 2 is a block diagram showing a vehicle occupant detection device according to an embodiment of the present invention;

DETAILED DESCRIPTION OF THE INVENTION

Figure 3:
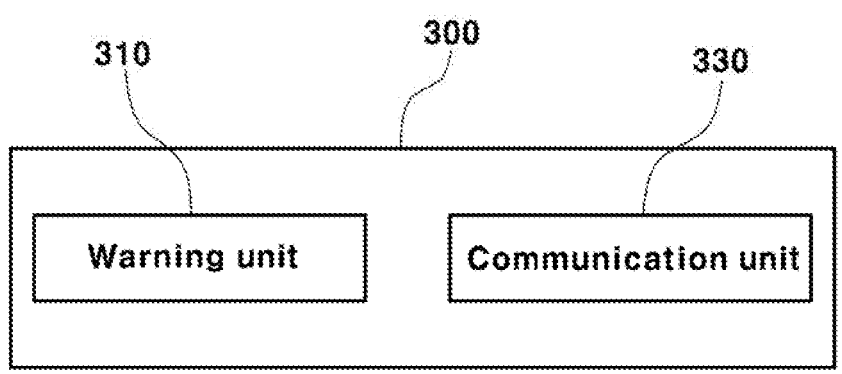
FIG. 3 is a block diagram showing an output unit of FIG. 2.

The advantages and features of the present invention and the manner of achieving them will become apparent with reference to the embodiments described in detail below with reference to the accompanying drawings. The present invention may, however, be embodied in many different forms and should not be construed as limited to the embodiments set forth herein. Rather, these embodiments are provided so that this disclosure will be thorough and complete and will fully convey the concept of the invention to those skilled in the art. Furthermore, the present invention is defined only by the scope of claims. Like reference numerals refer to like elements throughout the specification.

In addition, the embodiments described herein will be described with reference to cross-sectional views and/or plan views, which are ideal illustrations of the present invention. In the drawings, the thicknesses of the films and regions are exaggerated for an effective explanation of the technical content. Thus, the shape of the illustrations may be modified by manufacturing techniques and/or tolerances. Accordingly, the embodiments of the present invention are not limited to the specific shapes shown, but also include changes in shapes that are produced according to the manufacturing process. For example, the etching regions shown at right angles may be rounded or may have a shape with a certain curvature. Thus, the regions illustrated in the figures have schematic attributes, and the shapes of the regions illustrated in the figures are intended to illustrate specific types of regions of the elements and are not intended to limit the scope of the invention.

FIG. 1 is a view showing the inside of a vehicle in which a vehicle occupant detection device according to an embodiment of the present invention is installed, and FIG. 2 is a block diagram showing a vehicle occupant detection device according to an embodiment of the present invention.

Referring to FIGS. 1 and 2, the vehicle occupant detection device 1 may be installed inside the vehicle 10 to detect infants that are left inside the vehicle 10. When no guardians are present in the vehicle 10 and only infants are left inside the vehicle 10, the vehicle occupant detection device 1 detects the infant's biometric information and outputs a warning message to the outside of the vehicle 10. As a result, it is possible to notify the guardians or unspecified individuals outside the vehicle 10 that the infants are left in the vehicle 10.

The vehicle occupant detection device 1 may include a sensor unit 100, a control unit 200, an output unit 300, a database unit 400, and the temperature sensor 500. The vehicle occupant detection device 1 may be disposed in the front seat of the vehicle 10. Preferably, the vehicle occupant detection device 1 may be disposed in the driver's seat 11 of the vehicle 10. Specifically, the vehicle occupant detection device 1 may be disposed on a rear surface of the driver's seat 11, in which the rear surface may be a surface facing the driver's seat 11 in the rear seat 13.

The sensor unit 100 measures biometric information of the occupants located in the front seats 11 and 12 of the vehicle and the rear seat 13 of the vehicle 10. For example, the sensor unit 100 may be any one of an impulse-radio ultra-wideband (IR-UWB) communication sensor, a Lidar, a frequency modulated continuous wave (FMCW) radar, and a Doppler radar. Preferably, the first sensor unit 100 may be an IR-UWB communication sensor. The UWB communication refers to radio technology that uses a frequency band of 500 MHz or more, or is defined as a signal having a fractional bandwidth of at least 25%. The fractional bandwidth is a measure of bandwidth of the signal when comparing with its center frequency. The UWB communication is a radio technology that uses broadband frequencies, and has various advantages such as high range resolution, transmittance, strong immunity to narrowband noise, and coexistence with other devices sharing frequency. For example, the UWB communication has the advantage of detecting even minute movements of an object because of ultra-precise distance resolution characteristics of 1 cm or less.

An impulse-radio ultra-wideband radar (hereinafter, referred to as, "UWB radar") technology is a system in which the UWB communication technology is combined with radar and refers to a radar technology that transmits an very short duration-impulse signal having a wideband characteristic in a frequency domain and receives a signal reflected from objects and people thereby recognizing the surrounding situation. The UWB radar system generates an impulse signal with a time width of several nanoseconds to several picoseconds in the signal generator and emits the same at a wide angle or narrow band angle through a transmitting antenna. The emitted signal is reflected by various objects or people in the environment, and the reflected signal may be converted to a digital signal through a receiving antenna and an analog-to-digital converter (ADC).

Lidar emits a laser pulse and receives the laser pulse reflected back from the surrounding object to measure the distance from the laser to the object. Lidar may detect not only the distance to the object but also the velocity of the object and the shape of the object, and further may be used to generate a three-dimensional image around the object.

The biometric information includes at least one of heart rate, movement, or respiration of an occupant. The sensor unit 100 receives the signal reflected by the occupant and can detect the movement of the occupant's chest or abdomen, thereby sensing the heart rate or respiration of the occupant. In addition, the sensor unit 100 receives the reflected signal in real time and detects the movement of the occupant. Also, the sensor unit 100 receives the reflected signal in real time and detects the size and shape of the occupant. Therefore, the sensor unit 100 may detect biometric information such as heart rate, movement, or respiration of the occupant, and determine which seat the occupant is positioned inside the vehicle 10. The sensor unit 100 outputs a signal toward the occupant and receives the reflected signal from the occupant to measure the biometric information of the occupant. The sensor unit 100 may detect a plurality of occupants located in the front seats 11 and 12 and detect a plurality of passengers positioned in the rear seat 13. However, the sensor unit 100 may measure even movements of objects located within the vehicle 10.

A direction in which the sensor unit 100 outputs the signal may vary depending on a direction in which the vehicle occupant detection device 1 is installed. However, the sensor unit 100 may cover a range of −90 degrees to +90 degrees on the basis of a direction in which the vehicle occupant detection device 1 is installed, and a range of −90 degrees to +90 degrees in a direction opposite to the installed direction. That is, most of the signal output by the sensor unit 100 is output in the direction in which the vehicle occupant detection device 1 is installed, but a part of the signal may be output in a direction opposite to the direction in which the vehicle occupant detection device 1 is installed. Accordingly, the sensor unit 100 may detect biological signals or movements of an object within a range of 360 degrees on the basis of a position where the vehicle occupant detection device 1 is disposed. For example, the direction in which the vehicle occupant detection device 1 is installed may be a direction from the driver's seat 11 toward the rear seat 13, or the direction in which the rear surface of the driver's seat 11 faces. The range in which the sensor unit 100 detects the biometric information may be preset according to the size of the vehicle 10. It is possible to prevent the sensor unit 100 from detecting biometric information of an object (or a person) located outside the vehicle 10 by setting a detection range of the sensor unit 100 in advance.

The control unit 200 may analyze the biometric information measured by the sensor unit 100 to determine whether or not the occupant located inside the vehicle 10 is in a dangerous state. The control unit 200 may determine that the occupant located on the rear seat 13 is in a dangerous state when the biometric information is not detected in the front seats 11 and 12 but detected in the rear seat 13. For example, when the occupant located on the rear seat 13 is an infant, the control unit 200 may determine that the occupant is in a dangerous state. The control unit 200 may determine that the occupant located on the rear seat 13 is not in a dangerous state when the occupant is present in the front seats 11 and 12. In the case that the occupants are not present in the front seats 11 and 12, the control unit 200 may determine that the occupant is not in a dangerous state, when an occupant in the rear seat 13 is an adult, or there is an adult among occupants located in the rear seat 13. That is, when there is an adult among the occupants within the vehicle 10, the control unit 200 may determine that the infant located in the vehicle 10 is not in a dangerous state.

The control unit 200 may analyze the signal detected by the sensor unit 100 to determine whether the occupant is an adult or an infant. The signal output toward the occupant is reflected from the occupant and received by the sensor unit 100, and a pattern of the reflected signal may vary depending on the size and shape of the occupant. That is, the control unit 200 may analyze the reflected signal received by the sensor unit 100 to determine the size and shape of the occupant, and match the same with pre-stored data to determine whether the occupant is an adult or an infant. Herein, the sensor unit 100 may include one or more of an IR-UWB communication sensor, a Lidar, frequency-modulated continuous wave radar, and Doppler radar, and further include a thermal detecting sensor, and the like. Therefore, based on the signal detected by the sensor unit 100, the control unit 200 may determine whether the occupant is an adult or an infant. As another example, the control unit 200 may determine that a subject generating the biometric information is a pet. In this case, the control unit 200 may determine whether or not a pet is present in the vehicle 10.

The control unit 200 may output a signal containing a warning message to the outside of the vehicle 10 via the sensor unit 100 when it is determined that the occupant located inside the vehicle 10 is in a dangerous state. The signal containing the warning message may be the same as a signal that the sensor unit 100 outputs to measure the occupant's biometric information. For example, the signal containing the warning message may be a laser pulse signal or an impulse signal with ultra-wideband. The signal containing the warning message is transmitted to a terminal owned by any person outside the vehicle 10 so that any person may know that the infant has been left inside the vehicle 10 through the terminal. As a result, even if there is no configuration for outputting a separate warning message, the vehicle occupant detection device 1 may output the warning message to the outside of the vehicle 10. Accordingly, it is possible to reduce the cost of implementing the device for detecting a presence of an infant left in the vehicle 10, and to make the device compact.

The output unit 300 outputs a warning message when the control unit 200 determines that the occupant located inside the vehicle 10 is in a dangerous state. The output unit 300 outputs the warning message to the outside of the vehicle 10 through a warning sound or a warning light and transmits the warning message to a terminal located outside the vehicle 10 using a wireless communication method. The warning message output by the output unit 300 allows persons located outside the vehicle 10 to identify the presence of infants left in the vehicle 10.

The database unit 400 may store information needed to analyze information detected by the sensor unit 100 in the vehicle 10. As an example, the database unit 400 may include information used to distinguish occupant's movements from the other non-occupant movements among movements that may be detected within the vehicle 10. As another example, the database unit 400 may include information used to perceive an infant's movements among movements of a plurality of occupants that may be detected within the vehicle 10. The control unit 200 may analyze information detected by the sensor unit 100 on the basis of information stored in the database unit 400.

The temperature sensor 500 detects the temperature inside the vehicle 10. Depending on the temperature inside the vehicle 10, impacts on infants left in the vehicle 10 may vary. For example, when the temperature inside the vehicle 10 is 20 degrees Celsius, there is no problem in infant's health even though the infant may be left in the vehicle 10 alone for a short time. However, when the temperature inside the vehicle 10 is 40 degrees Celsius, serious health problems may occur in infant's health even if the infant is in vehicle 10 even for a short time. Accordingly, the temperature sensor 500 detects the temperature inside the vehicle 10 and transmits the temperature value to the control unit 200. At this time, the control unit 200 determines a point of time to output a warning message based on the temperature value. Specifically, the control unit 200 applies allowable time that takes to output the warning message differently to each of a case in which the temperature value is equal to or higher than a predetermined temperature and a case in which the temperature values is lower than the predetermined temperature. In this case, the allowable time may be a time interval from a point of time when the biometric information is not detected in the front seat but detected in the rear seat to a point of time when the warning message is output. For example, the control unit 200 may set the allowable time as 30 minutes when the temperature inside the vehicle 10 is 20 degrees Celsius, and the control unit 200 may set the allowable time as 5 minutes when the temperature inside the vehicle 10 is 40 degrees Celsius. As a result, it is possible to prevent situations where the warning message is output when the guardian leaves the vehicle 10 for a short time with leaving the infant in the vehicle 10. Generally, the allowable time may be set to be shorter as the temperature inside the vehicle 10 is higher, and also set to take into account the temperature outside the vehicle 10. That is, the temperature inside the vehicle 10 may fall below 10 degrees Celsius in winter, and thus the health of infants may be more fatal in winter. Therefore, the control unit 200 may set the allowable time in consideration of the temperature outside the vehicle 10 and the temperature inside the vehicle 10.

The vehicle occupant detection device 1 according to an embodiment of the present invention may determine when infants are left alone in the vehicle 10. When there is any occupant in the front seats 11 and 12, the vehicle occupant detection device 1 may determine that there is a guardian who protects the infant located in the rear seat 13 and thus the infant is not in a dangerous state. However, when there are any occupants in the front seats 11 and 12, the vehicle occupant detection device 1 determines that the infant in the rear seat 13 is in a dangerous state and thus outputs the warning message.

Also, since the vehicle occupant detection device 1 according to an embodiment of the present invention uses a Lidar or an ultra-wideband (IR-UWB) communication sensor, the occupant's biometric information may be accurately measured even in the vehicle 10 at a high temperature. Particularly, when the UWB communication sensor is used, the vehicle occupant detection device 1 may be operated at low power due to the characteristic of UWB communication.

In addition, the sensor unit 100 may detect both the front seats 11 and 12 and the rear seat 13 due to the characteristics of the sensor, even if only one sensor is provided in the vehicle 10, thereby reducing the cost consumed to implement a device for preventing infant from being left in the vehicle.

FIG. 3 is a block diagram showing an output unit of FIG. 2.

Referring to FIGS. 2 and 3, the output unit 300 may include a warning unit 310 and a communication unit 330.

The warning unit 310 may output a warning message to the outside of the vehicle 10 through a warning sound or a warning light. The warning unit 310 may include an interface capable of outputting a warning sound and a light source capable of producing a warning light.

The communication unit 330 may transmit a warning message to a terminal located outside the vehicle 10 using a wireless communication scheme. Herein, the terminal may be a terminal of a guardian of infants left inside the vehicle, or may be a terminal owned by each of unspecified individuals present outside the vehicle. When the terminal is the terminal of the guardian, the guardian may recognize that the infant is left inside the vehicle. When the terminal is the terminal owned by an unspecified individual, people outside the vehicle may recognize that the infant is left inside the vehicle and thus take separate actions. The wireless communication method may include a Bluetooth method, an RF method, a Near Field Communication (NFC) method, and the like. In addition, the wireless communication system may use a signal output by the sensor unit 100 to detect presence of the occupant. That is, the wireless communication method may be a method of outputting a signal through an IR-UWB communication sensor or a Lidar.

Figure 4:
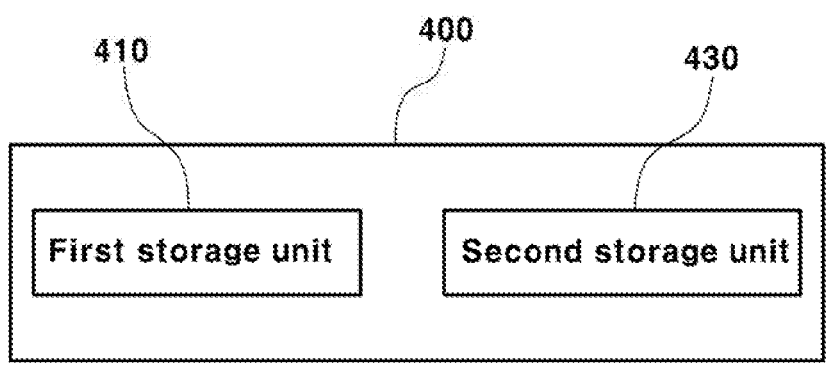
FIG. 4 is a block diagram showing a database unit of FIG. 2.
Figure 5A:
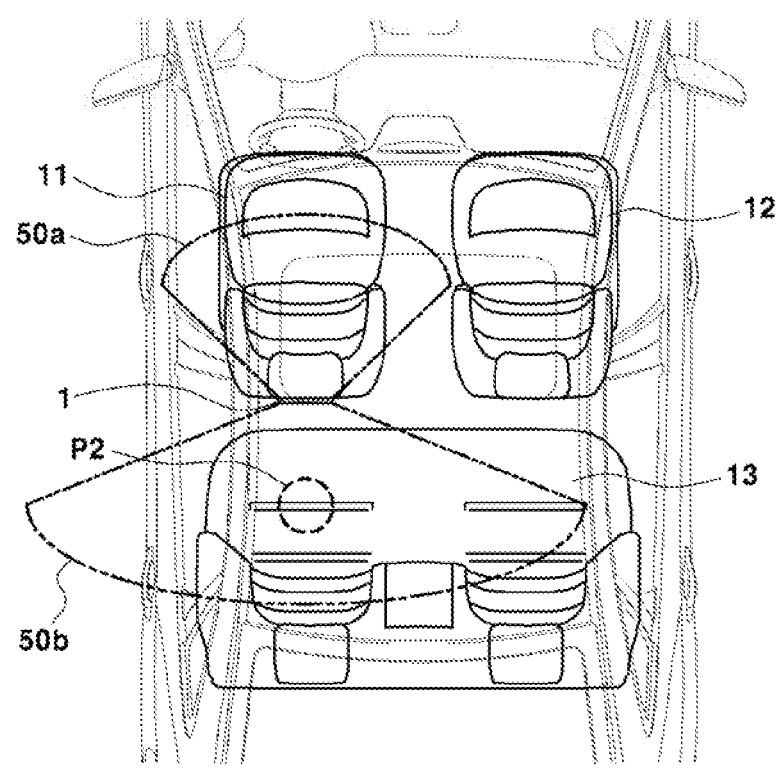
FIGS. 5A to 5D are top plan views showing the inside of a vehicle in which the vehicle occupant detection device according to embodiments of the present invention is installed.
Figure 5B:
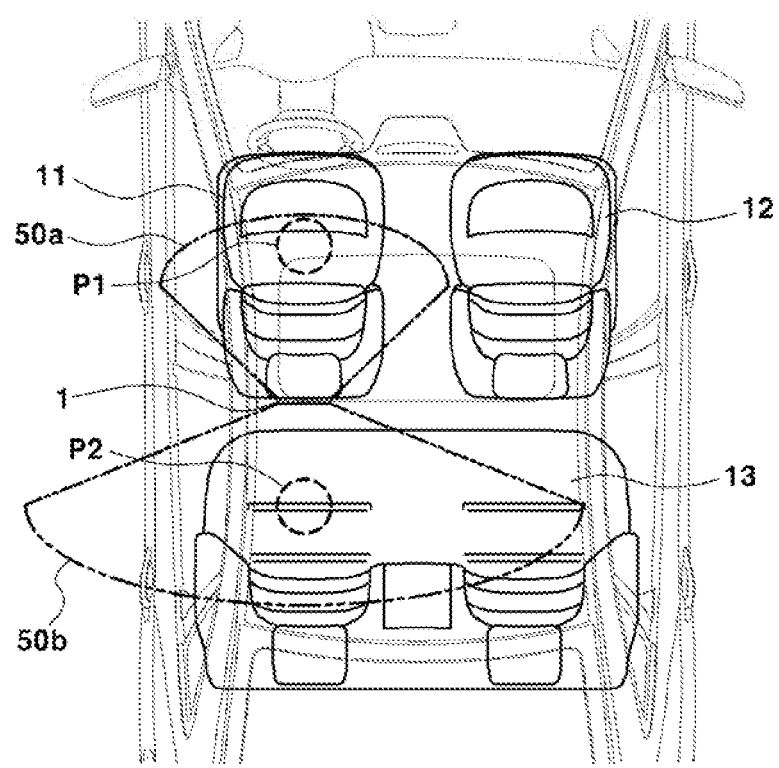
Figure 5C:
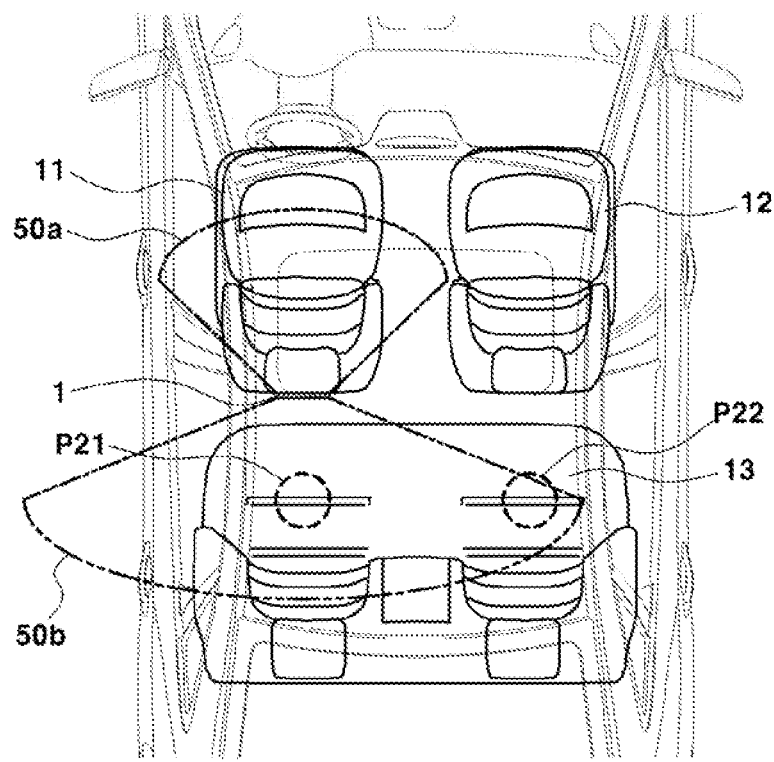
Figure 5D:
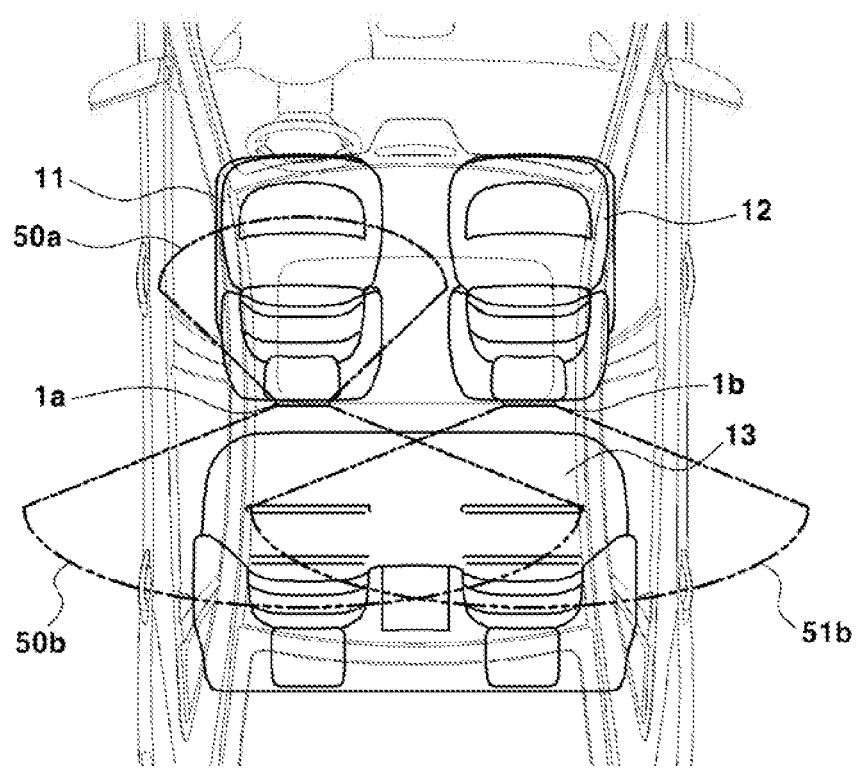

FIG. 4 is a block diagram showing a database unit of FIG. 2.

Referring to FIGS. 2 and 4, the database unit 400 may include a first storage unit 410 and a second storage unit 430. The database unit 400 stores information used by the control unit 200 to accurately analyze various information about the occupant in the vehicle using various information obtained through the sensor unit 100.

The first storage unit 410 may store information about repetitive movements that may occur within the vehicle. The repetitive movements may mean moving on a regular cycle. For example, the repetitive movements may include rotation of an electric fan, movement of a second hand of a clock watch, and the like. The control unit 200 determines that the same information as the information about the repetitive movement stored in the database unit 400 among the biometric information measured by the sensor unit 100 is not biometric information of the occupant. That is, the control unit 200 may perform an analysis by using only the occupant's biometric information among various information measured by the sensor unit 100.

The second storage unit 430 may store first information on the size, shape, etc. of a person obtained through machine learning, and second information on heart rate, respiration, and movement of a person. The control unit 200 may compare the biometric information measured by the sensor unit 100 with the first information and the second information stored in the database unit 400. This allows the control unit 200 to determine whether the occupant is an adult or an infant, and to determine whether the biometric information is indicative of heart rate of a person, respiration of a person, or movement of a person. The first information and the second information may be stored in advance in the database unit 400 so that it is possible to clarify what the biometric information measured by the sensor unit 100 means.

FIGS. 5A to 5D are top plan views showing the inside of a vehicle in which the vehicle occupant detection device according to embodiments of the present invention is installed. The occupant located in the driver's seat or in the front passenger seat is defined as a first occupant, and the occupant located in the rear seat is defined as a second occupant.

Referring to FIGS. 2 to 5A, the vehicle occupant detection device 1 may be disposed on the rear surface of the driver's seat 11 among the front seats 11 and 12. The sensor unit 100 may detect both a direction in which the vehicle occupant detection device 1 is disposed and a direction opposed to the direction in which the vehicle occupant detection device 1 is disposed. The direction in which the vehicle occupant detection device 1 is disposed may be a direction from the driver's seat 11 toward the rear seat 13. The sensing area of the sensor unit 100 is defined as a first area 50a in the direction opposite to the direction in which the vehicle occupant detection device 1 is disposed and the sensing area of the sensor unit 100 is defined as a second area 50b in the direction in which the vehicle occupant detection device 1 is disposed. The sensor unit 100 of the vehicle occupant detection device 1 may determine whether the occupant is present in the driver's seat 11 and determine whether the occupant is present on the rear seat 13. In this embodiment, the second occupant P2 is located on the rear seat 13 and the occupant is not located on the driver's seat 11. The sensor unit 100 detects the second area 50b to detect the presence of the second occupant P2. Herein, it is possible to know whether the second occupant P2 is an adult or an infant using the information stored in the database unit 400. The control unit 200 may detect that the first occupant P1 is not present and the second occupant P2 is present. When the control unit 200 determines that the second occupant P2 is an infant using information stored in the database unit 400, the control unit 200 may control the output unit 300 to output a warning message, and control the sensor unit 100 to output a signal containing the warning message.

Referring to FIGS. 2 to 5B, the vehicle occupant detection device 1 may be disposed on the rear surface of the driver's seat 11 among the front seats 11 and 12. In the present embodiment, the first occupant P1 is located on the driver's seat 11 and the second occupant P2 is located on the rear seat 13. The sensor unit 100 detects the first region 50a and the second region 50b to detect the presence of the first occupant P1 and the second occupant P2. The control unit 200 determines that the first occupant P1 and the second occupant P2 are present together in the vehicle, thereby not outputting the warning message.

Referring to FIGS. 2 to 5C, the vehicle occupant detection device 1 may be disposed on the rear surface of the driver's seat 11 of the front seats 11 and 12. In this embodiment, the second occupant P21 and the third occupant P22 are located on the rear seat 13 and no occupant is located on the driver's seat 11. The sensor unit 100 may detect the second region 50b to detect the presence of the second occupant P21 and the third the occupant P22. In this case, it is possible to know whether the second occupant P21 and the third occupant P22 are adults or infants using the information stored in the database unit 400. The control unit 200 may determine that the first occupant is not present and the second occupant P21 and the third occupant P22 are present. When the control unit 200 determines that the second occupant P21 and the third occupant P22 are both infants using information stored in the database unit 400, the control unit 200 controls the output unit 300 to output a warning message and controls the sensor unit 100 to output a signal containing the warning message. When the control unit 200 determines that at least one of the second occupant P21 and the third occupant P22 is an adult using information stored in the database unit 400, the control unit 200 controls the output unit 300 not to output the warning message. That is, the control unit 200 does not output the warning message when the infant is accompanied by an adult (guardian) even if the infant is located on the rear seat 13.

Referring to FIGS. 2 to 5D, two vehicle occupant detection devices 1a and 1b may be provided to the driver's seat 11 and the front passenger's seat 12, respectively. The vehicle occupant detection device 1a may detect the first region 50a and the second region 50b and the second vehicle occupant detection device 1b may detect the third region 51a and the fourth region 51b. The first vehicle occupant detection device 1a may detect both a direction in which the first vehicle occupant detection device 1a is disposed and a direction opposite to the direction in which the first vehicle occupant detection device 1a is disposed, and the occupant detection device 1b may detect both a direction in which the second vehicle occupant detection device 1b is disposed and a direction opposed to the direction in which the second occupant detection device 1b is disposed. The direction in which the first vehicle occupant detection device 1a is disposed may be a direction from the driver's seat 11 toward the rear seat 13 and the direction in which the second vehicle occupant detection device 1b is disposed is a direction from the front passenger's seat 12 toward the rear seat 13. The sensing area of the sensor unit 100 of the first vehicle occupant detection device 1a in a direction opposite to the direction in which the first occupant detection device 1a is disposed is defined as a first area 50a, the sensing area of the sensor unit 100 in a direction in which the first vehicle occupant detection device 1a is disposed is defined as a second area 50b. The sensing area of the sensor unit 100 of the second vehicle occupant detection device 1b in a direction opposite to a direction in which the second vehicle occupant detection device 1b is disposed is defined as a third area 51a, and the sensing area of the sensor unit 100 in a direction in which the vehicle occupant detection device 1b is disposed is defined as a fourth area 51b.

The first vehicle occupant detection device 1a and the second vehicle the occupant detection device 1b may detect the entire interior of the vehicle. The second vehicle occupant detection device 1b may determine the presence or absence of the occupant located in the passenger seat 12.

Even if any adult is not located in the driver's seat 11, the infants located on the rear seat 13 may not be exposed to a dangerous situation when an adult is located in the front passenger seat 12. Thus, both the first vehicle occupant detection device 1a and the second vehicle occupant detection device 1b may detect all the occupants located in the driver's seat 11 and the front passenger seat 12, respectively.

Unlike the above example, one vehicle occupant detection device 1 may detect the entire area inside the vehicle. That is, the entire interior of the vehicle may be detected depending on the detection range and the installation location of the vehicle occupant detection device 1. In addition, the position where the vehicle occupant detection device 1 is disposed may not be particularly limited. For example, the vehicle occupant detection device 1 may be embedded in the driver's seat 11 or the front passenger's seat, disposed in the ceiling inside the vehicle, and disposed between the driver's seat 11 and the front passenger's seat. That is, the sensing area of the sensor unit 100 may vary depending on the change of the placement position of the vehicle occupant detection device 1. More specifically, the area (first area) where the sensor unit 100 detects the first occupant and the area (second area) where the sensor unit 100 detects the second occupant can be changed depending on the placement position of the vehicle occupant detection device 1. However, even if the placement position of the vehicle occupant detection device 1 varies, it may be determined whether or not the infant located in the second area is left on the basis of whether or not there is an adult located in the first area.

Figure 6:
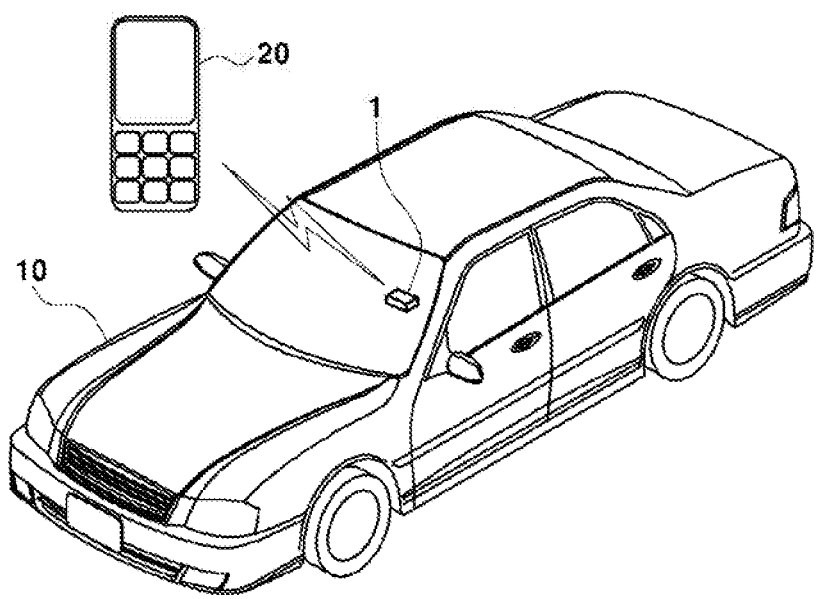
FIG. 6 is a diagram illustrating communication between a vehicle occupant detection device and a terminal outside the vehicle according to an embodiment of the present invention.

FIG. 6 is a diagram illustrating communication between a vehicle occupant detection device and a terminal outside the vehicle according to an embodiment of the present invention.

Referring to FIGS. 2 and 6, the vehicle occupant detection device 1 may communicate with a terminal 20 located outside the vehicle 10. In this case, the terminal 20 may be a terminal of a guardian of infants left inside the vehicle, or may be a terminal owned by each of unspecified individuals that are present outside the vehicle. The vehicle occupant detection device 1 may output a signal containing a warning message through the sensor unit 100 and output the warning message through the output unit 300. In this case, the sensor unit 100 may output a signal through an IR-UWB communication sensor or a Lidar, and the output unit 300 may output the warning message via a wireless communication method including a Bluetooth type, an RF type, and a Near Field Communication (NFC) method, and the like. However, the manner in which the output unit 300 communicates with the outside of the vehicle 10 may not be particularly limited.

According to an embodiment of the present invention, when the infant is left inside the vehicle 10, the vehicle occupant detection device 1 may output the warning message to the outside of the vehicle 10. Accordingly, the terminal 10 outside the vehicle 10 may receive the warning message, and the guardian or the unspecified person may be notified that the infant is left in the vehicle 10, through the terminal 10.

Figure 7:
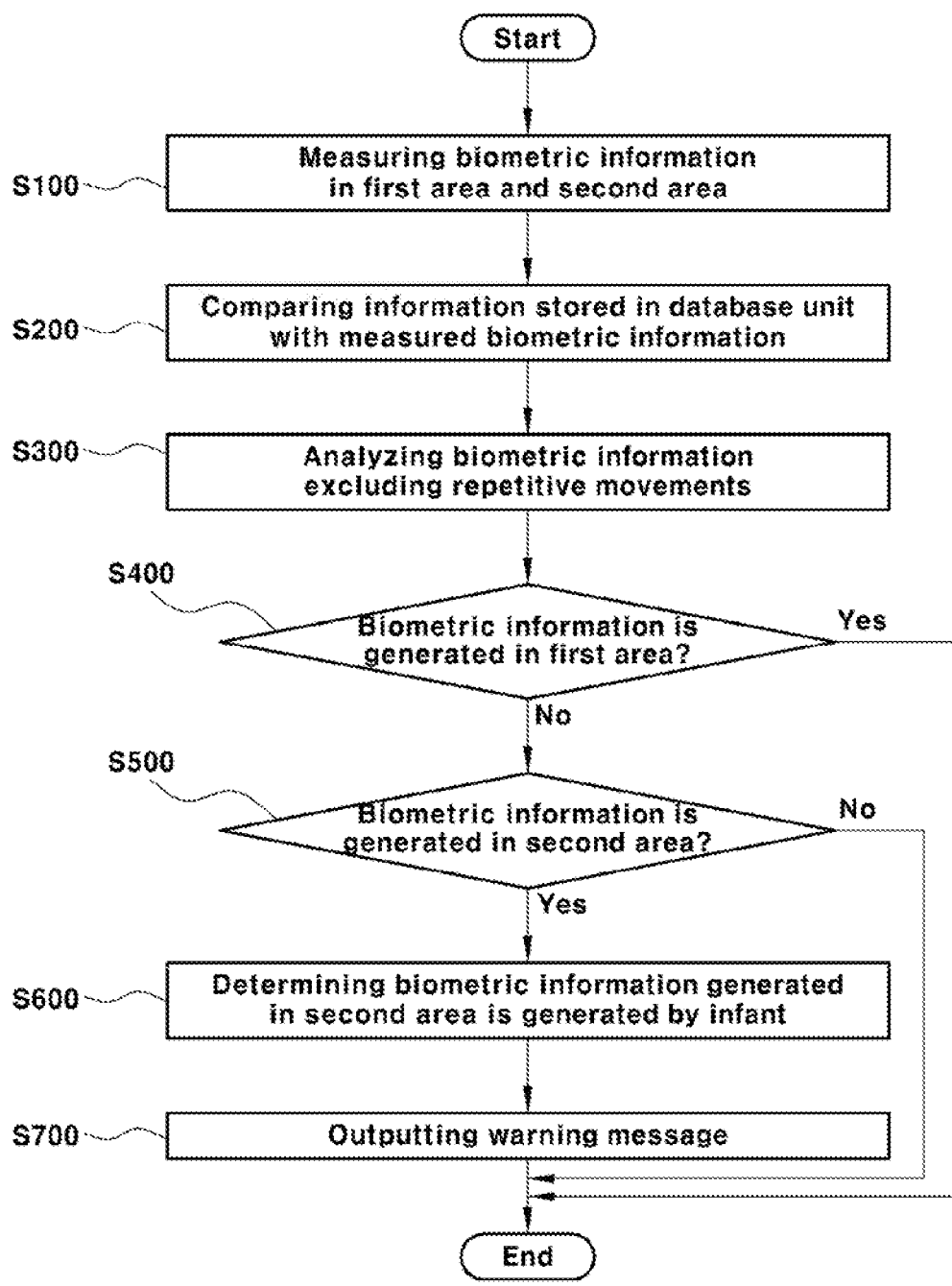
FIG. 7 is a flowchart illustrating a vehicle occupant detection method according to an embodiment of the present invention.

FIG. 7 is a flowchart illustrating a vehicle occupant detection method according to an embodiment of the present invention.

Referring to FIG. 7, the sensor unit of the vehicle occupant detection device may detect a first region and a second region inside the vehicle. The sensor unit may detect various information including biometric information generated in the first area and the second area. The first region may be a sensing region of a sensor unit that detects a driver's seat and a front passenger seat, and the second region may be a sensing region of a sensor unit that detects a rear seat. In the first area and the second area, it is possible to measure various information obtained by detecting movements of a machine, movements of a companion animal, etc., in addition to the biometric information (S100).

The control unit of the vehicle occupant detection device may compare the information stored in the database unit with the measured biometric information. The database unit may store information needed to analyze information detected by the sensor unit in the vehicle (S200).

The control unit may determine that the repetitive movements among information measured by the sensor unit are not caused by the occupant. The control unit may analyze the presence or absence of an infant and the presence or absence of an adult (guardian) among the occupants in the vehicle on the basis of only information excluding repetitive movements among the biometric information (S300).

The control unit may determine whether or not biometric information is generated in the first area. In this case, the biometric information is information excluding repetitive movement, and may be information generated only by the occupant. When the biometric information is generated in the first area, the control unit may control the output unit so as not to output the warning message. Generally, when biometric information is generated in the first area, an adult may be present in the vehicle (S400).

The control unit may determine whether biometric information is generated in the second area. When the biometric information is not generated in the second area, the control unit may control the output unit so as not to output the warning message. When the biometric information is generated in the second area, the control unit may determine that the occupant located inside the vehicle is in a dangerous state (S500).

The control unit may determine whether the biometric information generated in the second area is generated by an adult or an infant. The database unit may store information that determines whether the reflected signal received by the sensor unit is a signal reflected by an infant or an adult. That is, the signal reflected by the infant and the signal reflected by the adult may have different signal patterns. The reflected signal may mean that the signal output by the sensor unit is reflected by the occupant. The control unit may control the output unit so that the sensor unit does not output a warning message when the received signal is a signal reflected by an adult (S600).

When the signal received by the sensor unit is a signal reflected by the infant, the control unit may determine that the infant is left alone in the vehicle, and control the output unit to output a warning message (S700).

While the present invention has been described in connection with accompanying drawings, it will be understood by those skilled in the art that the present invention may be embodied in other specific forms without departing from the spirit or essential characteristics thereof. Therefore, it will be understood that the above-described embodiments are illustrative in all aspects and not restrictive.

What is claimed is:

1. A vehicle occupant detection device, comprising: a sensor unit disposed in a vehicle to detect biometric information of an occupant located in a front seat of the vehicle and a rear seat of the vehicle;
a control unit analyzing the biometric information measured by the sensor unit; and an output unit outputting a warning message on the basis of the information analyzed by the control unit, wherein the control unit determines that the occupant located in the rear seat is in a dangerous state when the biometric information is not detected in the front seat, but detected in the rear seat by the sensor unit, the sensor unit outputs a signal toward the occupant and receives the signal reflected from the occupant to measure the biometric information of the occupant, and the control unit determines whether the occupant is an adult or an infant through the reflected signal, the control unit determines the number of the occupants located in the rear seat when the biometric information is not detected in the front seats but detected in the rear seat, and the control unit determines whether the adult is present or not among a plurality of occupants, and wherein the control unit controls the output unit to output the warning message when the adult is not present among the occupants, the control unit controls the output unit not to output the warning message when the adult is present among the occupants.

2. The device of claim 1, wherein the biometric information is at least one of heart rate, movement, or respiration of the occupant.

3. The device of claim 1, wherein the sensor unit is any one of an impulse-radio ultra-wideband (IR-UWB) communication sensor, a Lidar, a frequency modulated continuous wave (FMCW) radar, and a Doppler radar.

4. The device of claim 3, wherein the sensor unit is attached to a rear surface of the front seat, and the rear surface is a surface facing the front seat in the rear seat.

5. The device of claim 1, wherein the sensor unit measures the biometric information generated in a first area and a second area, in which the first area is present in a direction facing the rear seat in the front seat and the second area is present in a direction opposite to the first area.

6. The device of claim 1, wherein the front, seat means a driver's seat; and the control unit determines whether a first occupant located in the driver's seat and a second occupant located in the rear seat are present or not, and controls the output unit to output the warning message when the first occupant is not present and the second occupant is present.

7. The device of claim 1, further comprising a database unit storing information on repetitive movements generated inside the vehicle, in which the control unit determines that information that is the same as the information stored in the database unit among the biometric information measured by the sensor unit is not the biometric information of the occupant.

8. The device of claim 7 wherein the repetitive movement means moving on a regular cycle.

9. The device of claim 1, wherein the control unit controls the output unit to output the warning message when determining that the occupant located in the rear seat is in a dangerous state.

10. The device of claim 9, wherein the output unit includes:

a warning unit outputting the warning message through a warning sound or a warning light; and a communication unit transmitting the warning message to a terminal located outside the vehicle through a wireless communication method.

11. The device of claim 1, wherein the control unit outputs a signal containing the warning message to the outside of the vehicle through the sensor unit, and the signal is the same as a signal that the sensor unit outputs to measure the biometric information.

12. The device of claim 1, wherein a range in which the sensor unit, detects the biometric information is set in advance according to a size of the vehicle.

13. The device of claim 7, wherein the database unit compares a reflected signal with a signal pattern learned through machine learning, and the control unit determines whether the occupant is an adult or an infant using the signal pattern matched with the reflected signal.

14. The device of claim 1, further comprising a 5 temperature sensor disposed within the vehicle, wherein the control unit applies an allowable time from a point of time when the biometric information is not detected in the front seat but detected in the rear seat to a point of time when the 'warning message is output, differently to each of a case in 10 which a value of the temperature sensor is equal to or higher than a predetermined temperature and a case in which the value is lower than the predetermined temperature.

* * * * *